(12) United States Patent
Hanada et al.

(10) Patent No.: US 6,833,354 B1
(45) Date of Patent: Dec. 21, 2004

(54) AGENT FOR THE TREATMENT OF BONE DISEASES

(75) Inventors: Keigo Hanada, Kyoto (JP); Yoshiyuki Hiyama, Kyoto (JP); Makoto Tamura, Kyoto (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 987 days.

(21) Appl. No.: 08/197,678

(22) Filed: Feb. 17, 1994

Related U.S. Application Data

(63) Continuation of application No. 07/809,758, filed on Dec. 18, 1991, now abandoned.

(30) Foreign Application Priority Data

Dec. 19, 1990 (JP) .............................................. 2-419168
May 28, 1991 (JP) .............................................. 3-152517

(51) Int. Cl.$^7$ ........................ A61K 38/18; C07K 14/50
(52) U.S. Cl. ........................................ 514/12; 530/399
(58) Field of Search ................................ 530/399, 350, 530/817; 514/12, 2

(56) References Cited

U.S. PATENT DOCUMENTS

| | | | | |
|---|---|---|---|---|
| 4,959,314 A | * | 9/1990 | Mark et al. ................. | 435/69.1 |
| 5,155,214 A | * | 10/1992 | Baird et al. ................. | 530/399 |

FOREIGN PATENT DOCUMENTS

| EP | 0320148 | 6/1989 |
|---|---|---|
| EP | PCTEP8901075 | 9/1989 |
| US | PCTUS8601879 | 9/1986 |
| US | PCTUS8804189 | 11/1988 |
| US | PCTUS8904821 | 11/1989 |
| WO | 89/04832 | * 6/1989 |

OTHER PUBLICATIONS

Story et al. *Biochem Biophy Res Comm* 142(3):702–9 (1987).*
Gimenez–Gallego et al. *Biochem Biophys Res Comm* 135(2):541–48 (1986).*
Prats et al *Proc Natl Acad Sci USA* 86:1836–40 (Mar. 1989).*
Sommer et al. *Biochem Biophy Res Comm* 144(2):543–50 (1987).*
Kurokawa et al. *FEBS Lett* 213(1):189–194 (Mar. 1987).*
Abraham et al. *EMBO J.* 5:2523–28 (1986).*
Ganong, W.F. Review of Medical Physiology, Chap. 21, pp. 326–337, Appleton & Lange, 14$^{th}$ ed., 1989.*
Simmons, D.J. Clin. Orthop. Rel. Res. 200:100–113, 1985.*
Dijke et al. Biotech. 7:793–798, 1989.*
Aspenberg et al. *Acta Orthop Scand* 60(4):473–76 (1989).*
Hauschlea et al. J. of Biol Chem 201(27):12665–74 (1986).*
Sullivan et al J of Biol Chem 200:2399–2403 (1985).*
Gospodorowicz et al. Endocrine Reviews 8(2): 95–114, 1987.
Aspenberg et al. Biol. Abstr. No. 89055692, 1989.

* cited by examiner

*Primary Examiner*—Christine J. Saoud
(74) *Attorney, Agent, or Firm*—Nixon & Vanderhye P.C.

(57) ABSTRACT

An object of the present invention is to provide a novel agent for the treatment of bone diseases which can shorten a period for curing various fractures including acceleration of bone formation for bone defect, can improve bone strength of united bones and can also improve reduced bone strength accompanied by various diseases. The agent comprises as an effective ingredient a basic fibroblast growth factor and/or its analogue.

11 Claims, 3 Drawing Sheets

× 32

× 32

SEQUENCE LISTING (1) GENERAL INFORMATION:

(iii) NUMBER OF SEQUENCES:    5

(2) INFORMATION FOR SEQ ID NO:1:

(i) SEQUENCE CHARACTERISTICS:
        (A) LENGTH:      146 AMINO ACIDS
        (B) TYPE:        AMINO ACID
        (D) TOPOLOGY:    LINEAR (ii) MOLECULE TYPE:  PEPTIDE (xi) SEQUENCE DESCRIPTION: SEQ ID NO:1:

```
Pro Ala Leu Pro Glu Asp Gly Gly Ser Gly Ala Phe Pro Pro Gly
1               5                   10                  15

His Phe Lys Asp Pro Lys Arg Leu Tyr Cys Lys Asn Gly Gly Phe
                20                  25                  30

Phe Leu Arg Ile His Pro Asp Gly Arg Val Asp Gly Val Arg Glu
                35                  40                  45

Lys Ser Asp Pro His Ile Lys Leu Gln Leu Gln Ala Glu Glu Arg
                50                  55                  60

Gly Val Val Ser Ile Lys Gly Val Cys Ala Asn Arg Tyr Leu Ala
                65                  70                  75

Met Lys Glu Asp Gly Arg Leu Leu Ala Ser Lys Cys Val Thr Asp
                80                  85                  90

Glu Cys Phe Phe Phe Glu Arg Leu Glu Ser Asn Asn Tyr Asn Thr
                95                  100                 105

Tyr Arg Ser Arg Lys Tyr Thr Ser Trp Tyr Val Ala Leu Lys Arg
                110                 115                 120

Thr Gly Gln Tyr Lys Leu Gly Ser Lys Thr Gly Pro Gly Gln Lys
                125                 130                 135

Ala Ile Leu Phe Leu Pro Met Ser Ala Lys Ser
                140                 145
```

(2) INFORMATION FOR SEQ ID NO:2:

(i) SEQUENCE CHARACTERISTICS:
        (A) LENGTH:      146 AMINO ACIDS
        (B) TYPE:        AMINO ACIDS
        (D) TOPOLOGY:    LINEAR (ii) MOLECULE TYPE:    PEPTIDE (xi) SEQUENCE DESCRIPTION: SEQ ID NO:2:

```
Pro Ala Leu Pro Glu Asp Gly Gly Ser Gly Ala Phe Pro Pro Gly
1               5                   10                  15

His Phe Lys Asp Pro Lys Arg Leu Tyr Cys Lys Asn Gly Gly Phe
                20                  25                  30

Phe Leu Arg Ile His Pro Asp Gly Arg Val Asp Gly Val Arg Glu
                35                  40                  45

Lys Ser Asp Pro His Ile Lys Leu Gln Leu Gln Ala Glu Glu Arg
                50                  55                  60

Gly Val Val Ser Ile Lys Gly Val Ser Ala Asn Arg Tyr Leu Ala
                65                  70                  75

Met Lys Glu Asp Gly Arg Leu Leu Ala Ser Lys Ser Val Thr Asp
                80                  85                  90
```

```
Glu Cys Phe Phe Phe Glu Arg Leu Glu Ser Asn Asn Tyr Asn Thr
                    95                  100             105

Tyr Arg Ser Arg Lys Tyr Thr Ser Trp Tyr Val Ala Leu Lys Arg
                    110             115             120

Thr Gly Gln Tyr Lys Leu Gly Ser Lys Thr Gly Pro Gly Gln Lys
                    125             130             135

Ala Ile Leu Phe Leu Pro Met Ser Ala Lys Ser
                    140             145

(2) INFORMATION FOR SEQ ID NO:3:

(i) SEQUENCE CHARACTERISTICS:
        (A) LENGTH:       154 AMINO ACIDS
        (B) TYPE:         AMINO ACIDS
        (D) TOPOLOGY:     LINEAR (ii) MOLECULE TYPE: PEPTIDE (xi) SEQUENCE DESCRIPTION: SEQ ID NO:3:

Ala Ala Gly Ser Ile Thr Thr Leu Pro Ala Leu Pro Glu Asp Gly
            -5                   1               5

Gly Ser Gly Ala Phe Pro Pro Gly His Phe Lys Asp Pro Lys Arg
        10              15              20

Leu Tyr Cys Lys Asn Gly Gly Phe Phe Leu Arg Ile His Pro Asp
        25              30              35

Gly Arg Val Asp Gly Val Arg Glu Lys Ser Asp Pro His Ile Lys
        40              45              50

Leu Gln Leu Gln Ala Glu Glu Arg Gly Val Val Ser Ile Lys Gly
        55              60              65

Val Cys Ala Asn Arg Tyr Leu Ala Met Lys Glu Asp Gly Arg Leu
        70              75              80

Leu Ala Ser Lys Cys Val Thr Asp Glu Cys Phe Phe Phe Glu Arg
        85              90              95

Leu Glu Ser Asn Asn Tyr Asn Thr Tyr Arg Ser Arg Lys Tyr Thr
        100             105             110

Ser Trp Tyr Val Ala Leu Lys Arg Thr Gly Gln Tyr Lys Leu Gly
        115             120             125

Ser Lys Thr Gly Pro Gly Gln Lys Ala Ile Leu Phe Leu Pro Met
        130             135             140

Ser Ala Lys Ser
        145

(2) INFORMATION FOR SEQ ID NO:4:

(i) SEQUENCE CHARACTERISTICS:
        (A) LENGTH:       7 AMINO ACIDS
        (B) TYPE:         AMINO ACID
        (D) TOPOLOGY:     LINEAR (ii) MOLECULE TYPE:   PEPTIDE (xi) SEQUENCE DESCRIPTION:  SEQ ID NO:4:

Ala Gly Ser Ile Thr Thr Leu
-5

(2) INFORMATION FOR SEQ ID NO:5:

(i) SEQUENCE CHARACTERISTICS:
        (A) LENGTH:       11 AMINO ACIDS
        (B) TYPE:         AMINO ACID
        (C) TOPOLOGY:     LINEAR
```

```
    (ii) MOLECULE TYPE:      PEPTIDE (xi) SEQUENCE DESCRIPTION:  SEQ ID NO:5:

Gly Thr Met Ala Ala Gly Ser Ile Thr Thr Leu
-10                 -5
```

AGENT FOR THE TREATMENT OF BONE DISEASES

This application is a continuation of Ser. No. 07/809,758 filed Dec. 18, 1991, now abandoned.

BACKGROUND OF THE INVENTION

1. Field of the Invention

The present invention relates to an agent for the treatment of bone diseases such as traumatic fracture, fatigue fracture, pathologic fracture as well as, for example, reduction in bone strength accompanied by various diseases and inhibition of bone formation accompanied by disease

2. Statement of the Prior Art

For the treatment of traumatic fracture or fatigue fracture, a method is utilized for repositioning (or repositing) and fixing an injured site and then allowing the natural healing ability of the patient to occur. In natural healing of fractured bone, bone union requires a number of days, e.g., about 2 weeks for metacarpal bone, about 5 weeks for forearm bone and about 12 weeks for neck of femur, on the average. In this case, pharmacological treatment is not usually performed but nutritional treatment such as an administration of calcium, is done, if necessary and desired.

Furthermore in pathologic fracture resulting from osteoporosis, diabetes, etc., the natural healing ability of a patient is lowered and hence, in addition to the reposition and fixing of an injured site, pharmacological treatment, an administration of estrogen or calcitonin, etc., is applied; or the above pharmacological treatment is performed in combination with the nutritional treatment. The pharmacological treatments or those in combination with nutritional treatment are also applied to the treatment of reduced bone strength resulting from diseases such as osteoporosis or diabetes.

Under the actual circumstance that fracture treatment has been left to the natural healing-ability of the patient himself, development of an oral agent for accelerating fracture healing comprising 24,25-dihydroxycholecalciferol was recently reported: the agent is useful as a drug for shortening the period of fracture healing (Japanese Patent Application KOKAI No. 63-310828). Reports have been also made on agents for the treatment of bone diseases such as an agent for accelerating bone formation, comprising rentinan (Japanese Patent Application KOKAI No. 63-17828), an agent for the treatment of bone diseases comprising at least one agent selected from the group consisting of chitin, chitosan and derivatives thereof (Japanese Patent Application KOKAI No. 63-156726), as new drugs for shortening a period for fracture healing or improving reduced bone strength accompanied by various diseases; or an agent comprising physiologically active ganglioside of retina, and the like (Japanese Patent Application KOHYO No. 63-502035).

The basic fibroblast growth factor (hereinafter abbreviated as bFGF) is a peptidic cell growth factor which was confirmed to be present in pituitary, brain, retina, corpus luteum, adrenal, kidney, placenta, prostate and thymus. It is known that bFGF induces the proliferation of mesodermal cells including vascular endothelial cells ["Cell Growth Factor Part II", edited by Tissue Culture Association, Japan, pages 15 to 20, published by Asakura Publishing Co.). In recent years, bFGF has been also isolated from cartilage and bone [J.B.C., 260, 2399–2403 (1985); ibid., 261, 12665–12674 (1986)].

It was expected that the bFGF would effectively accelerate the fracture healing, since bFGF evokes a proliferation of mesodermal cells including vascular endothelial cells and is present in cartilage or bone. The in vivo test on bone formation reveals that bFGF accelerates bone formation only in combination with decalcified bovine bone containing a bone growth factor [Act. Orthop. Scand., 60, 473–476 (1989)]. bFGF has a high structural similarity to an acidic fibroblast growth factor which accelerated callus formation in fractured ends at the early stage of fracture healing but inhibited the matrix synthesis of cartilage or bone and was thus evaluated to be inferior to the control group, in bone strength at the site of callus formation [J. Orthopaedic Res., 8, 364–371 (1990)]. bFGF is also recognized to have a high similarity to the acidic fibroblast growth factor in view of the action in vivo.

In the trend of the studies on bFGF as described above, the present inventors have developed drugs for the first time, which can accelerate callus formation at a fracture site by application of bFGF alone, accelerate bone formation for bone defect, promote bone union, improve the strength at a fracture site and increase the bone strength.

SUMMARY OF THE INVENTION

The present invention has been made in view of the actual situation of aforementioned treatment for bone diseases, and an object of the present invention is to provide a novel agent for the treatment of bone diseases which can shorten the healing period of various fractures including acceleration of bone formation for bone defects, improve bone strength of fused bones and also improve reduced bone strength accompanied by various diseases.

As a result of extensive investigation to accomplish the aforesaid object, the present inventors have succeeded in developing useful drugs as agents for the treatment of bone diseases using a basic fibroblast growth factor (bFGF) and have come to complete the present invention.

That is, the agent for the treatment of bone diseases of the present invention is characterized by comprising as an effective ingredient a basic fibroblast growth factor (bFGF) and/or an analogue thereof.

DETAILED DESCRIPTION OF THE PREFERRED EMBODIMENTS

Figure 1:
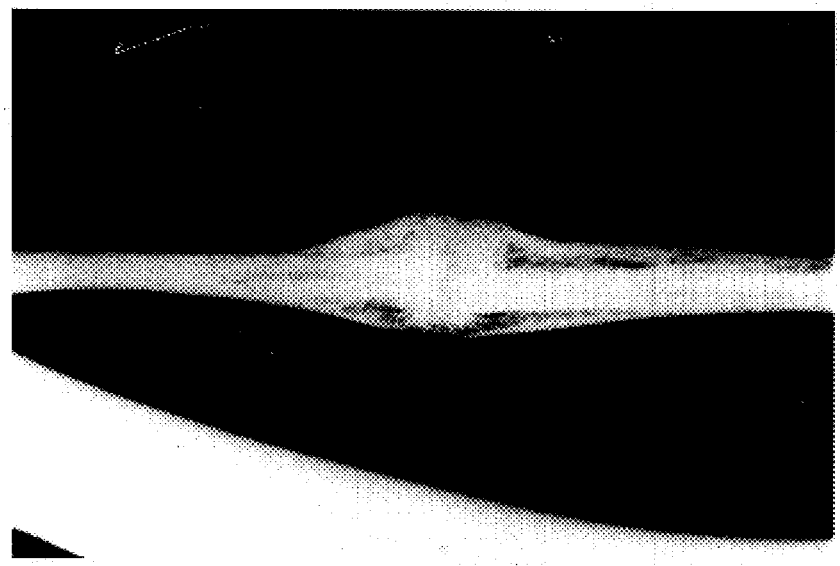
FIG. 1 shows a soft X-ray photograph (×2.3 times) of fractured bone (left fibula) in Group B of Example 1 three weeks after fracture in Example 1.

Hereinafter the present invention is described in detail.

bFGF as the effective ingredient of the agent for the treatment of bone diseases in accordance with the present invention is a well known growth factor as described above and its presence is confirmed in human, bovine, mouse, rat, and other mammals. Basically, bFGF from any animal origin has the same activity in vivo. However, where the agent of the present invention for the treatment of bone diseases is applied to humans, it is particularly preferred to use bFGF having the same amino acid sequence as that of bFGF produced in the human body (hereinafter referred to as human bFGF), in view of antigenicity.

Furthermore in the agent of the present invention for the treatment of bone diseases, the analogue of bFGF may be also used. Herein the bFGF analogue is used to refer to polypeptide of (1) or (2) described below.

(1) This refers to polypeptide comprising substantially the same amino acid sequence as that of bFGF produced in a specific mammal. Substantially the same amino acid sequence refers to an amino acid sequence in which 1 to 6 amino acids are substituted with different amino acids. The resultant polypeptide maintains the biological activity of bFGF.

(2) This refers to polypeptide in which a supplemental amino acid segment(s) is/are added to bFGF produced in a specific mammal at the N terminus and/or the C terminus, or to the polypeptide (1) described above at the N terminus and/or the C terminus. The supplemental amino acid segment refers to a segment which comprises 1 to 12 amino acids and does not damage the biological activity of bFGF or the biological activity of the polypeptide (1) described above.

Human, bFGF is a polypeptide comprising 146 amino acids shown in the Sequence Listing as having Sequence ID No. 1. In the agent of the present invention for the treatment of bone diseases, for example, a polypeptide comprising 146 amino acids shown in the Sequence Listing as having Sequence ID No. 2 may be also used as the analogue of human bFGF (analogue of the polypeptide (1) described above). In the polypeptide of Sequence ID No. 2, 69 cysteine (Cys) and 87 cysteine (Cys) which constitute the amino acid sequence of human bFGF are substituted with serine (Ser), respectively.

As the analogue of polypeptide (2) described above, for example, a polypeptide comprising 154 amino acids shown in the Sequence Listing as having Sequence ID No. 3 may be also used. In the polypeptide, a segment comprising 8 amino acids is added to human bFGF at the N terminus. Furthermore, for example, a polypeptide comprising 153 amino acids shown in the Sequence Listing as having Sequence ID No. 4 in which a segment comprising 7 amino acids is added to human bFGF at the N terminus, may be also used as the analogue of polypeptide (2) described above. Similarly, a polypeptide comprising 147 amino acids added with Met at the N terminus or a polypeptide comprising 157 amino acids added with a segment comprising 11 amino acids shown in the Sequence Listing as having Sequence No. 5 attached at the N terminus may be also used.

In the agent of the present invention for the treatment of bone diseases, bFGF and its analogues may be used singly or in combination. The bFGF analogues include a plurality of substances. These analogues may be also used singly or in combination.

In order to supply the agent of the present invention for the treatment of bone diseases stably on an industrial scale, it is particularly preferred to produce bFGF or its analogues in a microorganism such as $E.$ $coli$, etc. or in a cultured cell by genetic recombination technology available to one of ordinary skill in the art since bFGF is present in vivo in an extremely trace amount.

The agent of the present invention for the treatment of bone diseases comprises as an effective ingredient bFGF and/or its analogue described above. Specific forms of the agent include a solution comprising bFGF and/or its analogue, physiological saline or other conventional auxiliary agents (glucose, sucrose, buffer, etc.), an injection or a spray using the solution, a gel, an ointment, etc. The agent of the present invention for the treatment of bone diseases may take a route of topical application or general application, but topical application is particularly preferred.

The agent of the present invention for the treatment of bone diseases is applicable to A through E described below.
A. Various traumatic fractures
B. Various fatigue fractures
C. Pathologic fracture
   a. Fracture accompanied by osteoporosis primary osteoporosis (senile, postmenopausal, juvenile) secondary osteoporosis {(hyperthyroidism, Cushing's syndrome (caused by steroid administration), acromegalia, hypogonadism [hypopituitarism, Klinfelter's syndrome, Turner's syndrome], osteogenesis imperfecta, hypophosphatasia, homocystinuria, immobilization osteoporosis, diabetes}
   b. Fracture accompanied by osteomalacia
   c. Fracture accompanied by malignant tumor
   d. Fracture accompanied by multiple myeloma
   e. Fracture accompanied by osteogenesis inperfect acongenita
   f. Fracture accompanied by osteocystoma
   g. Fracture accompanied by suppurative osteomyelitis
   h. Fracture accompanied by osteopetrosis
   i. Fracture accompanied by nutrition disorder
D. Reduction in bone strength accompanied by various diseases (e.g., diseases shown in C. above)
E. Inhibition of bone formation accompanied by various diseases (e.g., diseases shown in C. above)

An effective dose of the agent for the treatment of bone diseases in accordance with the present invention varies depending the kind of application, degree of bone diseases, age or condition of the patient, etc. but is generally in the range of about 0.1 $\mu$g to 10 mg/fracture site, as the effective ingredient, in the case of fracture. Generally for the purpose of accelerating healing, a particularly preferred route for application is to administer the agent in direct contact with the fracture site. However, the agent may also be subcutaneously applicable or directly injectable around the fracture site.

The agent for the treatment of bone diseases in accordance with the present invention may be also applied to the treatment of bone diseases of domestic animals, pet mammals, raised wild animals, etc. In this case, for example, bovine bFGF and/or its analogue may be used. The same preparation forms and effective dose as in the case of humans can apply.

Hereinafter the present invention is described with reference to the examples listed below.

EXAMPLE 1

Five (5) to six (6) SD strain male rats (weighing 300 to 325 g) of 10 weeks of age were in one group, and 9 groups in total were prepared. Sodium pentobarbital solution (concentration of 50 mg/ml, trademark: NENBUTAL, manufactured by Dainippon Pharmaceutical Co., Ltd.) was intraperitoneally administered to each animal in a dose of 0.20 ml to anesthesize. Then, the hair at the left lower limb was cut and the skin and the muscular layer were incised in a length of 1 cm to expose the fibula. The fibula was cut out at the center, using bone scissors.

The 3 groups were used as control groups. After the cut fibula was repositioned with tweezers, 36 µl of 0.1 M phosphate buffered saline was dropped onto the repositioned site and the incised skin was sutured. After diluted iodine tincture was applied to the wound after operation, 0.1 ml of 10-fold physiological saline dilution of sodium penicillin G-streptomycin sulfate solution [penicillin concentration of 10000 U/ml, streptomycin concentration of 10000 µg/ml, manufactured by Gibco Co.] was subcutaneously administered.

The remaining 6 groups were used as the groups of this invention. In 3 groups (hereinafter referred to as Group A of Example 1) out of the 6 groups, 36 µl of a human bFGF solution (concentration: 0.5 µg/ml) was dropwise applied to each animal, instead of 36 µl of 0.1 M phosphate-buffered saline. Said human bFGF solution was previously prepared by diluting with 0.1 M phosphate-buffered saline, a solution (concentration of 3.3 mg/ml) of human bFGF (polypeptide shown by Sequence ID No. 3; hereinafter human bFGF refers to this polypeptide throughout the specification) expressed in $E.\ coli$, which had been obtained by known methods of genetic recombination technology. Thereafter the groups were otherwise treated in a manner similar to the control groups.

In the remaining 3 groups of this invention (hereinafter referred to as Group B of Example 1), 36 µl of a human bFGF solution (concentration: 50 µg/ml) obtained by diluting a solution (concentration: 3.3 mg/ml) of human bFGF with 0.1 M phosphate-buffered saline was dropwise applied to each animal, instead of 36 µl of the human bFGF solution (concentration: 0.5 µg/ml) used in Group A of Example 1, and the groups were treated otherwise in a manner similar to Group A of Example 1.

One group was chosen from the control groups (3 groups in total), Group A of Example 1 (3 groups in total) and Group B of Example 1 (3 groups in total) every 1, 2 and 3 other weeks after fracture. Each animal in the groups chosen was anesthesized with ether and bled from the carotid artery to death. The right and left leg bones were withdrawn and immediately immersed in 10% neutral formalin buffer to fix them.

Using these fixed specimens, the following items were determined.

(a) Determination of Cross Sectional Area of Fractured Callus

After fixing with 10% neutral formalin buffer, photographs of the leg bones (tibia and fibula) were taken by soft X rays (trademark of equipment used: SOFTEX-CMB, manufactured by Japan Softex Co., Ltd., conditions: 24–30 kV, 1–3 mA) to prepare soft X ray pictures. From the pictures, photographs enlarged to 10 times with a stereoscopic microscope were prepared. Based on these photographs, the cross sectional area of callus was determined using an image analysis device [trademark: Oscondigitizer Model SQ-3100F, manufactured by PHOTORON Co.].

(b) Determination of Callus Volume

After fixing with 10% neutral formalin buffer, the volume of the left and right fibulae (left: fractured bone, right: normal bone) was determined, respectively, with a device for measuring volume [trademark, PLETHYSMOMETER, manufactured by Ugo Basile Co., Ltd.]. A value obtained by subtracting the measurement data of the right fibula from that of the left fibula was determined to be the volume of callus.

(c) Determination of Bone Mineral Content (BMC) and Bone Mineral Density (BMD) of Fractured Callus After fixing with 10% neutral formalin buffer, BMC of the left and right fibulae (left: fractured bone, right: normal bone) was determined, respectively, with a device for measuring BMC [trademark, Model DCS-600, manufactured by Aloka Co., Ltd.]. A value obtained by subtracting the measurement data of the right fibula from that of the left fibula was determined to be the BMC of callus. Furthermore, BMD of the left and right fibulae were determined, respectively, using the same device and BMD was determined in a manner similar to the case of the BMC of callus.

(d) Biomechanical Analyses for Fractured Fibula

After the left and right fibulae were withdrawn 3 weeks after fracture and fixed in 10% neutral formalin buffer, break energy in the specimens thus obtained was determined, with a device for measuring bone metabolism [trademark, RHEOROMETER MAX, manufactured by Iio Electric Co., Ltd.]. Furthermore, a ratio (percentage) in bone strength of the left fibula (fractured bone) to that of the right fibula (normal bone) was determined as an increment of bone strength.

(e) Histological Examination

After fixing in 10% neutral formalin buffer for a week, the left and right fibulae were decalcified with 10% EDTA (ethylenediamine tetraacetate) solution for 10 days, respectively. After decalcification, the bones were washed with water for 12 hours and embedded in paraffin in a conventional manner, from which sliced tissue sections each having a thickness of 1 to 4 µm were prepared by a microtome, respectively. Then, each specimen was stained with hematoxylin-eosine. The stained specimens were microscopically examined and pictures of them were taken.

In these results, the results on measurements of cross sectional area, volume, BMC, and BMD of callus and the results of test on bone strength of the fractured bones are shown in Table 1.

TABLE 1

| | | Cross-sectional area of callus (mm²) | Callus volume (mm³) | BMC of callus (mg) | BMD of callus (mg/cm²) | Bone strength (10⁵ erg/cm³) | | |
|---|---|---|---|---|---|---|---|---|
| | | | | | | Normal bone | Fractured bone | Increment (%)*¹ |
| Group A of Example 1 (0.5 μg bFGF) | 1 week | 9.0 ± 2.9 | 50.4 ± 22.0 | 3.9 ± 0.8 | 4.2 ± 2.4 | — | — | — |
| | 2 weeks | 7.8 ± 1.0 | 32.0 ± 10.6 | 7.1 ± 2.3 | 7.3 ± 2.2 | — | — | — |
| | 3 weeks | 7.8 ± 1.3 | 17.6 ± 6.2 | 7.4 ± 1.4 | 7.4 ± 1.6 | 0.30 ± 0.0 | 0.08 ± 0.02 | 28.5 ± 11.6 |
| Group B of Example 1 (50 μg bFGF) | 1 week | 10.4 ± 2.9 | 59.2 ± 22.7 | 3.9 ± 2.2 | 3.5 ± 1.9 | — | — | — |
| | 2 weeks | 15.7 ± 2.6 | 55.2 ± 19.5 | 11.7 ± 3.7 | 12.2 ± 3.5 | — | — | — |
| | 3 weeks | 12.0 ± 3.1 | 38.8 ± 14.2 | 12.6 ± 3.0 | 14.0 ± 3.3 | 0.43 ± 0.22 | 0.18 ± 0.1 | 77.7 ± 22.4 |
| Control group | 1 week | 6.2 ± 1.0 | 31.6 ± 13.0 | 2.8 ± 1.2 | 3.5 ± 1.9 | — | — | — |
| | 2 weeks | 7.2 ± 1.0 | 32.4 ± 9.3 | 5.7 ± 1.7 | 6.0 ± 2.2 | —*² | — | — |
| | 3 weeks | 5.4 ± 1.4 | 16.0 ± 3.1 | 5.9 ± 2.5 | 5.9 ± 2.5 | 0.53 ± 0.23 | 0.10 ± 0.02 | 21.6 ± 7.3 |

*Numerical values in the table indicate (mean value as the group) ± (standard deviation)
*¹Numerical values indicate (mean value) ± (standard deviation) of data calculated from [(bone strength of fractured bone)/(bone strength of normal bone)] × 100
*²(mean value) ± (standard deviation) of 3 subjects As is evident from Table 1, the cross sectional area of callus and callus volume one week after fracture increased in Group A of Example 1 and Group B of Example 1, as compared to the cross sectional area of callus and callus volume in the control groups. On and after one week, both the cross sectional area of callus and callus volume gradually decreased both in the groups of this invention and in the control groups, but the cross sectional area of callus and callus volume were larger in the groups of this invention even 3 weeks after. These results reveal that the agent of the present invention for the treatment of bone diseases accelerates the callus formation.

Further with respect to BMC and BMD of fractured callus, no remarkable difference was noted between the groups of the present invention and the control groups one week after fracture. In the groups of the present invention, however, both BMC and BMD increased to about 2.3 times that of the control groups. These results reveal that the agent of the present invention for the treatment of bone diseases has an excellent effect on fracture healing. This is also evident from the fact that in Groups A and B of Example 1, the increment in the test on bone strength after 3 weeks is higher than in the control groups.

Furthermore, the above mentioned higher increment in the test on bone strength indicates that the agent of the present invention for the treatment of bone diseases is excellent in the activity of improving the bone strength or the strength at the fracture site of bone.

The results stated above are clear also from the soft X-ray photographs, some of which are attached as the drawings.

In the soft X-ray photograph in Group B of Example 1 taken one week after fracture, a large callus image is noted and the formation of new bone having weak transmittance is recognized beneath the periosteum around the fractured site of fibula. Turning to a soft X-ray photograph in the control group taken one week after fracture, the formation of callus having strong transmission is noted but its area is smaller than in Group B of Example 1.

Figure 2:
FIG. 2 shows a soft X ray photograph (×2.3 times) of fractured bone (left fibula) in the control group three weeks after fracture in Example 1.

FIG. 1 shows a soft X-ray photograph in Group B of Example 1 taken 3 weeks after fracture. In the photograph, the transmission of callus decreases indicating that new bone formation is markedly accelerated. Turning to FIG. 2 which shows a soft X-ray photograph of the control group taken 3 weeks after fracture, decreased transmission of callus means a formation of new bone but its degree is smaller than in Group B of Example 1.

It is also evident from the results of histopathological survey that the agent of the present invention for the treatment of bone diseases promotes callus formation and exhibits an excellent effect on bone formation.

That is, as is clear from a microscopic photograph (×5 times) of the sliced tissue sections, proliferation of cartilage, proliferation of osteogenic mesenchymal cells derived from periosteum, etc., and formation of fibrous new bone around fractured site are remarkable. On the other hand, as is clear from a microscopic photograph in the control group one week after fracture, proliferation of cartilage, proliferation of osteogenic mesenchymal cells, and formation of fibrous new bone around fractured site are also noted in the control group one week after fracture but their degrees are smaller than in Group B of Example 1.

Further as is clearly seen from a microscopic photograph in Group B of Example 1 three weeks after fracture, osteogenic mesenchymal cells showed marked proliferation within an enlarged callus and the fracture ends are united by a number of newly formed fibrous bones but cartilage slightly remains around fracture site. Formation of marrow cavity is also noted between the fibrous new bones. On the other hand, as is clear from a microscopic photograph in the control group 3 weeks after fracture, callus itself is small and formation of cartilage is poor in the control group 3 weeks after fracture. In addition, the fracture ends are still separated by cartilage.

EXAMPLE 2

Firstly, five (5) to six (6) SD strain male rats (weighing 300 to 325 g) of 10 weeks age were as one group and 6 groups in total were prepared. In the same manners as in Example 1, sodium pentobarbital solution (concentration of 50 mg/ml, trademark: NENBUTAL, manufactured by Dainippon Pharmaceutical Co., Ltd.) was intraperitoneally administered to each animal in a dose of 0.20 ml to anesthesize. Then, the hair at the left lower limb was cut and the skin and the muscular layer were incised in a length of 1 cm, respectively, to expose the fibula. The fibula was cut out at the center using bone scissors.

Two groups out of the 6 groups were used as control groups and treated in a manner similar to the control groups in Example 1.

The remaining 4 groups were used as the groups of this invention. In 2 groups (hereinafter referred to as Group A of Example 2) out of the 4 groups, 36 µl of a human bFGF solution (concentration: 1 µg/ml) obtained by diluting with o.1 M phosphate-buffered saline, a solution (concentration: 3.3 mg/ml) of human bFGF prepared in a similar manner to Example 1 was dropwise applied to each animal, instead of 36 µl of the human bFGF solution (concentration: 0.5 µg/ml) used in Group A of Example 1, and the groups were treated otherwise in a manner similar to Group A of Example 1.

In the remaining 2 groups of this invention (hereinafter referred to as Group B of Example 2), 36 µl of a human bFGF solution (concentration: 100 µg/ml) obtained by diluting with 0.1 M phosphate buffered saline, a solution (concentration: 33 mg/ml) of human bFGF prepared in a similar manner to Example 1 was dropwise applied to each animal, instead of 36 µl the human bFGF solution (concentration: 1 µg/ml) of used in Group A of Example 2, and the groups were treated otherwise in a manner similar to Group A of Example 2.

One group was chosen from the control groups (2 groups in total), Group A of Example 2 (2 groups in total) and Group B of Example 2 (2 groups in total) every 1 and 3 other weeks after fracture. The right and left leg bones were treated in a manner similar to Example 1 to prepare specimens fixed in 10% neutral formalin buffer.

Then, the cross sectional area of callus, callus volume, BMC and BMD of callus were determined in a manner similar to Example 1. These measurement results are shown in Table 2.

TABLE 2

| | Cross sectional area of callus (mm$^2$) | Callus volume (mm$^3$) | BMC of callus (mg) | BMD of callus (mg/cm$^2$) |
|---|---|---|---|---|
| Group A of Example 2 (1 µg of bFGF): | | | | |
| 1 week | 9.5 ± 2.6 | 58.5 ± 22.9 | 4.3 ± 0.5 | 3.9 ± 0.4 |
| 3 weeks | 7.9 ± 1.7 | 26.5 ± 7.0 | 4.6 ± 2.2 | 6.4 ± 3.0 |
| Group B of Example 2 (100 µg of bFGF): | | | | |
| 1 week | 10.5 ± 1.3 | 49.5 ± 7.5 | 2.5 ± 1.5 | 3.0 ± 2.0 |
| 3 weeks | 8.7 ± 1.5 | 24.5 ± 7.5 | 9.4 ± 1.3 | 9.6 ± 2.1 |
| Control group: | | | | |
| 1 week | 6.7 ± 1.2 | 32.0 ± 4.0 | 0.6 ± 0.5 | 1.4 ± 0.9 |
| 3 weeks | 5.6 ± 0.7 | 13.6 ± 8.4 | 3.0 ± 1.6 | 3.3 ± 1.8 |

*Numerical values in the table indicate:
(mean value in the group) ± (standard deviation)

As is evident from Table 2, the measurement results in Example 2 have the same tendency as those in Example 1, indicating that the agent of the present invention for the treatment of bone diseases accelerates callus formation and excellent effect on fracture healing.

EXAMPLE 3

Firstly, many male rats of SD strain (weighing 300 to 325 g) of 10 weeks age were prepared and a solution of streptozotocin (concentration of 40 mg/ml) in sodium citrate buffer (pH=4.9) was intravenously administered through the tail vein in a dose of 0.1 ml/100 g of body weight.

Then, one week after the administration of streptozotocin, the blood sugar level of each animal was determined by the method for measuring absorbance using a blood sugar measurement kit (trademark: NEW BLOOD SUGAR TEST, manufactured by Boehringer Yamanouchi Co., Ltd.). Rats showing a blood sugar level of 250 mg/dl or more were chosen as model rats for diabetes. Five (5) or six (6) rats were placed into one group and 8 groups in total were prepared.

Further five (5) or six (6) SD strain male rats (weighing 300 to 325 g) of 10 weeks age were grouped in one, and 2 groups as total were prepared for non-diabetes control group.

Then the left fibula was cut out at the center using bone scissors in a manner similar to Example 1.

Among 8 groups of model rats for diabetes, 4 groups were made control. With respect to each animal in 2 groups (hereinafter referred to as Control Group A) out of these 4 groups, the cut fibula was repositioned with tweezers followed by suture of the incised skin, application of diluted iodine tincture to the wound in operation and subcutaneous administration of 10-fold dilution of sodium penicillin G-streptomycin sulfate with physiological saline to the sutured site in a manner similar to Example 1.

In the remaining 2 groups (hereafter referred to as Control Group B) in the control groups, 36 µl of the gel of 0.1 M phosphate buffer (pH 6.5) containing fibrinogen, aprotinin and thrombin in concentrations of 41.6 mg/ml, 0.41 mg/ml and 33.3 U/ml, respectively, were dropwise applied to each animal, instead of 36 µl of 0.1 M phosphate-buffered saline in the control group of Example 1. The groups were treated otherwise in a manner similar to the control group of Example 1.

The remaining 4 groups of model animals for diabetes were made the groups of this invention. In 2 groups (hereinafter referred to as Group A of Example 3) out of the 4 groups, 36 µl of the gel further containing 0.5 µg/ml of human bFGF was dropwise applied to each animal, instead of 36 µl of the gel in Control Group B. The animal was treated otherwise in a manner similar to Control Group B.

In the remaining 2 groups of this invention (hereafter referred to as Group B of Example 3), 36 µl of the gel further containing 0.5 µg/ml of human bFGF was dropwise applied to each animal, instead of 36 µl of the gel in Control Group B. The animal was treated otherwise in a manner similar to Control Group B.

One group was chosen from Control Group A (2 groups in total), Control Group B (2 groups in total), Group A of Example 3 (2 groups in total), Group B of Example 3 (2 groups in total) and non-diabetes control groups (2 groups in total) every 1 and 3 other weeks after fracture. The right and left leg bones were treated in a manner similar to Example 1 to prepare-specimens fixed in 10% neutral formalin buffer.

Then, volume, BMC and BMD of fracture callus were determined in a manner similar to Example 1. Furthermore, histopathological examination was performed. In these results, the measurement data on the cross sectional area of callus, volume, BMC and BMD of callus are shown in Table 3.

TABLE 3

|  | Callus volume (mm³) | BMC of callus (mg) | BMD of callus (mg/cm²) |
|---|---|---|---|
| Group A of Example 3 (0.5 µg of bFGF): | | | |
| 1 week | 27.2 ± 11.5 | 2.3 ± 1.0 | 1.9 ± 1.0 |
| 3 weeks | 6.5 ± 3.0 | 2.6 ± 0.2 | 2.8 ± 1.3 |
| Group B of Example 3 (50 µg of bFGF): | | | |
| 1 week | 51.6 ± 8.1 | 4.2 ± 1.5 | 3.9 ± 1.2 |
| 3 weeks | 26.0 ± 5.8 | 7.8 ± 2.0 | 11.3 ± 1.7 |
| Control group A: | | | |
| 1 week | 17.2 ± 4.6 | 0.2 ± 0.1 | 0.4 ± 0.2 |
| 3 weeks | (6,10)*1 | (1.3,1.2)*1 | (3.1,1.7)*1 |
| Control group B: | | | |
| 1 week | 15.5 ± 8.0 | 2.6 ± 0.1 | 2.7 ± 0.5 |
| 3 weeks | 6.0 ± 2.0 | 1.7 ± 0.5 | 2.5 ± 0.9 |
| Non-diabetes control group: | | | |
| 1 week | 26.3 ± 7.2 | 2.2 ± 1.4 | 1.9 ± 0.8 |
| 3 weeks | 11.3 ± 3.5 | 4.2 ± 2.2 | 4.6 ± 2.2 |

*Numerical values in the table indicate:
(mean value in the group) ± (standard deviation)
*1Each measurement value of the two animals As is evident from Table 3, the measurement results in Example 3 have the same tendency as those in Example 1 and Example 2. The results reveal that the agent of the present invention for the treatment of bone diseases accelerates callus formation and excellent bone formation effect also in model rats for diabetes. Therefore, the agent of the present invention for the treatment of bone diseases has the activity of accelerating callus formation and exhibits excellent bone formation effect also in pathologic fracture.

These effects are evident also from soft X-ray photographs, some of which are attached as the drawings.

In a soft X-ray photograph in Group B of Example 3 one week after fracture, a large callus image is noted, whereas the callus image noted in a soft X-ray photograph in Control Group B one week after fracture is small and formation of callus is very poor.

Figure 3:
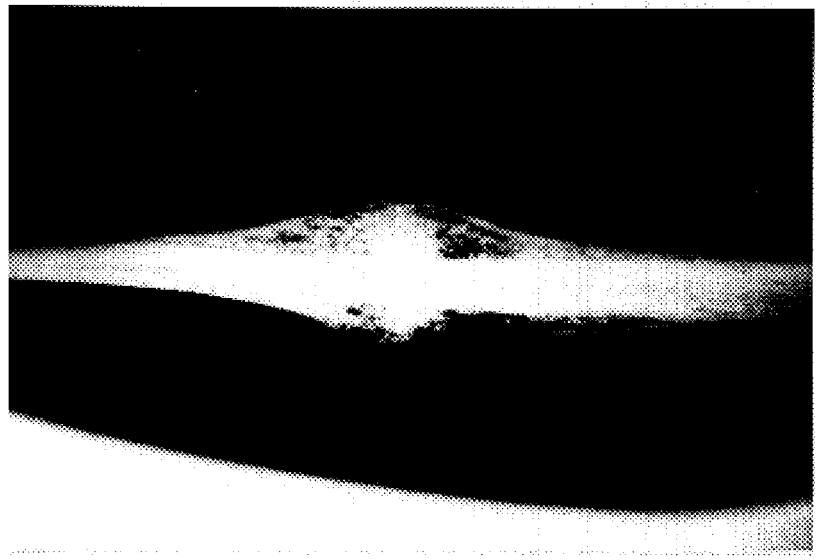
FIG. 3 shows a soft X ray photograph (×2.3 times) of fractured bone (left fibula) in Group B of Example 3 three weeks after fracture in Example 3.
Figure 4:
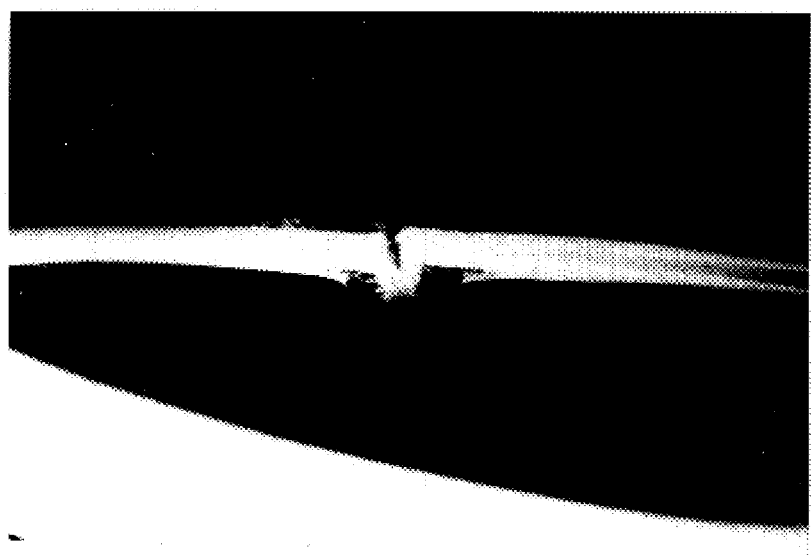
FIG. 4 shows a soft X ray photograph (×2.3 times) of fractured bone (left fibula) in Control Group B three weeks after fracture in Example 3.

Further in a soft X-ray photograph (3 weeks after fracture) of Group B of Example 3 which is attached as FIG. 3, formation of many bones are noted in a large callus, indicating the sign that union of the fracture site has started. To the contrary, no marked enlarge of callus is noted in a soft X-ray photograph (3 weeks after fracture) in Control Group B which is attached as FIG. 4. Union at the fracture site is not noted, either.

It is evident also from histopathological examination that the agent of the present invention for the treatment of bone diseases promotes callus formation and an excellent effect on fracture healing also in diabetic animal model.

That is, as is clearly seen from the microscopic photograph (×5 times) of sliced tissue sections, callus formation, cartilage formation and proliferation of osteogenic mesenchymal cells are remarkable in Group B of Example 3 one week after fracture. To the contrary, in a microscopic photograph of sliced tissue section in Control Group B taken one week after fracture, callus formation, cartilage formations, and proliferation of osteogenic mesenchymal cells are also noted in Control Group B one week after fracture but cartilage and osteogenic mesenchymal cells are poorer than in Group B of Example 3.

Further as is clear from the microscopic photograph of sliced tissue section, the fracture ends are still separated by cartilage or mesenchymal cells in Group B of Example 3 three weeks after fracture, but formation of new fibrous bones is remarkable and the fracture site has begun to be united from the periphery of callus. To the contrary, as is clear from a microscopic photograph of sliced tissue section, in Control Group B taken three weeks after fracture, the fracture site is still separated by the connecting tissue including osteogenic mesenchymal cells, and fromation of cartilage and fibrous new bones are poor.

EXAMPLE 4

Firstly five (5) SD strain male rats (weighing 300 to 325 g) of 10 weeks of age were grouped as one, and two groups were prepared. Prednisolone was subcutaneously administered to each animal of these groups twice every other day in a dose of 25 mg/kg (as 0.5% carboxymethyl cellulose aqueous solution). These groups are hereinafter referred to as steroid-administered rat groups. On the day following the second administration, each animal was operated as described below to prepare model rat with bone defect.

Furthermore, five (5) SD strain male rats (one group, weighing 300 to 325 g) of 10 weeks of age were separately prepared. The 0.5% carboxymethyl cellulose aqueous solution was subcutaneously administered to each animal of these groups twice every other day instead of prednisolone described above. This group is hereinafter referred to as non-steroid-administered rat group. On the day following the second administration, each animal was operated as described below to prepare model rat with bone defect.

Operation (Model Rat with Bone Defect)

After each animal was anesthesized in a manner similar to Example 1, the hair at the right lower limb was cut and the skin and the muscular layer were incised in a length of 1 cm to expose the front of the tibia. Then a hole having a diameter of 1.6 mm which reached the bone marrow was made using a dental drill, at the site of 1 cm from the tibial condyle of each animal, to prepare model animal with bone defect.

After the operation, 2 µl of the gel prepared from fibrinogen, aprotinin and thrombin prepared in a manner similar to Example 3 was dropwise applied to the bone defect site (hole made by a dental drill; hereinafter the same) of each animal in the non-steroid-administered rat group (hereinafter referred to as Control Group 4A) and in one steroid-administered rat group (hereinafter referred to as Control Group 4B) of each animal. After the application, the incised skin was sutured and diluted iodine tincture was applied to the wound after operation. Then a solution of penicillin G-streptomycin sulfate solution was subcutaneously given to the sutured site in a manner similar to Example 1.

In the remaining one steroid-administered rat group (hereafter referred to as Group of Example 4), 2 µl of the gel further containing 2 µg of human bFGF was dropwise applied (dose of human bFGF: 2 µg/bone defect site) to the bone defect site of each animal, instead of the gel applied to Control Group 4A. After the application, each animal was treated as in Control Group 4A.

After the operation, prednisolone was subcutaneously administered to each animal in Group of Example 4 and in Control Group 4B in the dose described above, three times in total on the next day and Days 3 and 5 after the operation. In Control Group 4A, 0.5% carboxymethyl cellulose aqueous solution was subcutaneously administered in the dose described above to each animal three times in total on the next day and Days 3 and 5 after the operation.

One week after the operation, a specimen of the right tibia from each animal which had been fixed in 10% neutral formalin buffer was prepared in a manner similar to Example 1. After a sliced tissue section was prepared in a manner similar to Example 1, each specimen was subjected to Masson's trichrome staining. The specimen was microscopically examined histopathologically and photographed. The results of histopathological examination is shown in Table 4.

TABLE 4

|  | Degree of bone formation* (number of animal) | | |
|---|---|---|---|
|  | – or + | ++ | +++ |
| Group of Example 4 | 0 | 3 | 2 |
| Control group 4A | 0 | 1 | 4 |
| Control group 4B | 4 | 1 | 0 |

*Symbols in the degree of bone formation denote the following:
–no bone formation
+slight bone formation
++moderate bone formation
+++remarkable bone formation As is clear from Table 4, moderate or remarkable bone formation was noted at the bone defect site of each animal in Group of Example 4, namely, the steroid-treated rat group administered with human bFGF. To the contrary, bone formation was hardly noted at the bone defect site in many rats in Control Group 4B, namely the steroid-treated rat group to which no human bFGF had been administered. On the other hand, natural healing proceeded normally in Control Group 4A which was the non-steroid-treated rat group and bone formation was markedly noted at the bone defect site in many rats. These results reveal that the agent of the present invention for the treatment of bone diseases has an excellent effect of accelerating bone formation also at the bone defect site of rat treated with steroid (corresponding to model animal with dysfunction of bone formation).

The above results are noted more clearly by comparing microscopic photographs (×10 times) of sliced tissue sections in the respective groups, some of which are attached as the drawings.

Figure 5:
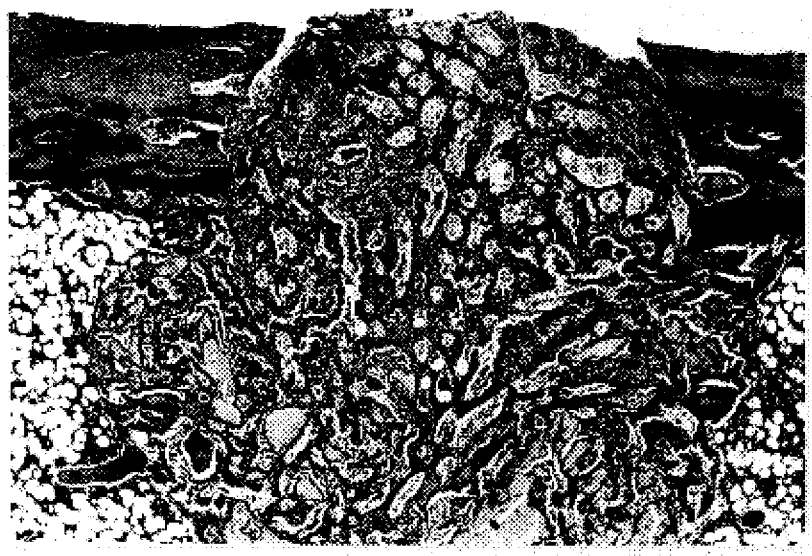
FIG. 5 shows a microscopic photograph (×32, taken from the subject showing conspicuous bone formation) of a sliced tissue section of the defect of (right tibila) in Group of Example 4 one week after bone defect in Example 4.
Figure 6:
FIG. 6 shows a microscopic photograph (×32, taken from the subject showing slight bone formation) of a sliced tissue section of the defect (right tibila) in Control Group 4B one week after bone defect in Example 4.

Comparing, for example, the microscopic photograph (of animal showing remarkable bone formation) in Group of Example 4 which is attached as FIG. 5 and the microscopic photograph (of animal showing moderate bone formation) in Group of Example 4 which is not attached with the microscopic photograph (of animal showing slight bone formation) in Control Group 4B which is attached as FIG. 6, slight new bones are merely noted at the bone defect site of the microscopic photograph of Control Group 4B shown in FIG. 6, whereas large amounts of new bones are noted at the bone defect site of the microscopic photograph of Group of Example 4, shown in FIG. 5 and of the microscopic photograph of Group of Example 4 which is not attached. Further comparison between the microscopic photograph shown in FIG. 5 and the microscopic photograph (of animal showing remarkable bone formation) in Control Group 4A which is not attached reveals that FIG. 5 shows healing image almost equal to that of the microscopic photograph of Control Group 4A not attached. From these results, it is evident that the agent of the present invention for the treatment of bone diseases possesses the excellent effect of accelerating bone formation.

EXAMPLE 5

In addition to human bFGF, the gel of human bFGF analogue (polypeptide shown by Sequence ID No. 2 obtained from E. coli by genetic recombination technology was used. Volume, bone mineral content (BMC) and bone mineral density (BMD) of fracturee callus were assessed in a similar manner to the case of Example 3.

These results (3 weeks after fracture) were presented in Table 5.

TABLE 5

|  | Callus volume (n) (mm$^3$) | BMC of callus (mg) | BMD of callus (mg/cm$^2$) |
|---|---|---|---|
| Group A of Example 5 (50 μg of bFGF): | 20.2 ± 7.2(6) | 7.1 ± 0.6 | 9.8 ± 2.1 |
| Group B of Example 5 (50 μg of bFGF anologue): | 22.3 ± 6.1(5) | 6.9 ± 1.1 | 9.1 ± 2.8 |
| Control group A: | 6.8 ± 3.8(5) | 2.6 ± 1.5 | 2.4 ± 1.3 |
| Control group B: | 10.4 ± 4.5(5) | 2.9 ± 1.7 | 4.1 ± 2.1 |
| Non-diabetes control group: | 8.8 ± 2.2(5) | 4.2 ± 2.6 | 5.8 ± 4.0 |

As is clear from Table 5, volume, BMC and BMD of bFGF analogue group (Group B of Example 5) were as large as those of bFGF group (Group A of Example 5), indicating that human bFGF analogue has an equivalent effect to bFGF of the present invention.

Toxicity

Six (6) male mice weighing 22 to 25 g were grouped in one, and a plurality of groups were subjected to test on toxicity. Human bFGF solution (concentration of 3.3 mg/ml) equivalent to those used in Examples 1 through 4 was subcutaneously administered to each animal in a dose corresponding to the body weight. Based on mortality 72 hours after, $LD_{50}$ value was determined.

As the result, the $LD_{50}$ value of human bFGF was 75 mg/kg or more.

As stated above, according to the present invention, there is provided a novel agent for the treatment of bone diseases which can shorten the healing period of various fractures including acceleration of bone formation for bone defect, and can improve reduced bone strength accompanied by various diseases.

What is claimed is:

1. A method of accelerating bone callus formation in vertebrates suffering from a bone disease comprising administering thereto an effective amount of a composition consisting essentially of the basic fibroblast growth factor of SEQ ID NO: 3.

2. The method according to claim 1, wherein the bone disease is selected from the group consisting of a fracture accompanied by osteoporosis, a fracture accompanied by osteomalacia, a fracture accompanied by malignant tumor, a fracture accompanied by multiple myeloma a fracture accompanied by osteogenesis imperfect acongenita, a fracture accompanied by osteocystoma, a fracture accompanied by suppurative osteomyelitis, a fracture accompanied by osteopetrosis and a fracture accompanied by nutrition disorder.

3. A method of increasing bone mineral content (BMC) of fractured bone callus in vertebrates suffering from bone fracture comprising administering thereto an effective amount of a composition consisting essentially of the basic fibroblast growth factor of SEQ ID NO: 3.

4. The method according to claim 3, wherein the bone fracture is selected from the group consisting of traumatic fracture, a fatigue fracture and a pathologic fracture.

5. The method according to claim 4, wherein the pathologic fracture is a fracture accompanied by a disease selected from the group consisting of osteoporosis, hypophosphatasia, homocystinuria, immobilization osteoporosis, and diabetes osteomalacia, a malignant tumor, multiple myeloma, osteogenesis imperfect acongenita, osteocystoma, suppurative osteomyelitis, osteopetrosis and a fracture accompanied by nutrition disorder.

6. A method of increasing bone mineral density of fractured bone callus in vertebrates suffering from bone fracture comprising administering thereto an effective amount of a composition consisting essentially of basic fibroblast growth factor of SEQ ID NO: 3.

7. The method according to claim 6, wherein the bone fracture is selected from the group consisting of a traumatic fracture, a fatigue fracture and a pathologic fracture.

8. The method according to claim 7, wherein the pathologic fracture is a fracture accompanied by a disease selected from the group consisting of osteoporosis consisting of a fracture accompanied by osteoporosis, a fracture accompanied by osteomalacia, a fracture accompanied by malignant tumor, a fracture accompanied by multiple myeloma a fracture accompanied by osteogenesis imperfect acongenita, a fracture accompanied by osteocystoma, a fracture accompanied by suppurative osteomyelitis, a fracture accompanied by osteopetrosis and a fracture accompanied by nutrition disorder.

9. A method of increasing bone strength of fractured bone callus in vertebrates suffering from bone fracture comprising administering thereto an effective amount of a composition consisting essentially of the basic fibroblast growth factor of SEQ ID NO: 3.

10. The method according to claim 9, wherein the bone fracture comprises traumatic fracture, fatigue fracture and/or pathologic fracture.

11. The method according to claim 10, wherein the pathologic fracture is a pathogenic fracture accompanied by a disease selected from the group consisting of osteoporosis, hypophosphatasia, homocystinuria, immobilization osteoporosis, and diabetes osteomalacia, a malignant tumor, multiple myeloma, osteogenesis imperfect acongenita, osteocystoma, suppurative osteomyelitis, osteopetrosis and a fracture accompanied by nutrition disorder.

* * * * *